US011429847B2

(12) United States Patent
Perkins et al.

(10) Patent No.: US 11,429,847 B2
(45) Date of Patent: Aug. 30, 2022

(54) SYSTEMS, METHODS, AND MEDIA FOR DECODING OBSERVED SPIKE COUNTS FOR SPIKING CELLS

(71) Applicant: The Trustees of Columbia University in the City of New York, New York, NY (US)

(72) Inventors: Sean Perkins, New York, NY (US); Mark Churchland, New York, NY (US); Karen Schroeder, San Diego, CA (US); John Patrick Cunningham, New Paltz, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/589,716

(22) Filed: Jan. 31, 2022

(65) Prior Publication Data

US 2022/0245434 A1 Aug. 4, 2022

Related U.S. Application Data

(60) Provisional application No. 63/210,441, filed on Jun. 14, 2021, provisional application No. 63/143,568, filed on Jan. 29, 2021.

(51) Int. Cl.
*G06N 3/06* (2006.01)
*A61B 5/00* (2006.01)
*G06N 3/04* (2006.01)

(52) U.S. Cl.
CPC .......... *G06N 3/061* (2013.01); *A61B 5/4064* (2013.01); *A61B 5/7225* (2013.01); *G06N 3/049* (2013.01)

(58) Field of Classification Search
CPC ...... G06N 3/049; A61B 5/4064; A61B 5/7225
See application file for complete search history.

(56) References Cited

U.S. PATENT DOCUMENTS 7,058,445 B2 6/2006 Kemere et al.
7,442,212 B2 * 10/2008 Richmond ................ A61F 2/72
623/25

(Continued)

FOREIGN PATENT DOCUMENTS

WO WO 20200152359 1/2020

OTHER PUBLICATIONS

Vyas, Saurabh, et al. "Computation through neural population dynamics." Annual Review of Neuroscience 43 (2020): 249-275. (Year: 2020).*

(Continued)

*Primary Examiner* — Benjamin P Geib
(74) *Attorney, Agent, or Firm* — Byrne Poh LLP

(57) ABSTRACT

Mechanisms including: receiving a first set of observed spike counts (FSoOSCs) for the spiking cells; determining a set of probabilities (SoPs) by: retrieving the SoPs from stored information (SI); or calculating the SopS based on the SI, wherein the SI regards possible biological states (BSs) of a subject, wherein each of the possible BSs belongs to at least one of a plurality of time sequences (PoTSs) of BSs, wherein each of the PoTSs of BSs corresponds to a possible action of the subject, and wherein each probability in the set of probabilities indicates a likelihood of observing a possible spike count for one of the plurality of spiking cells; identifying using a hardware processor a first identified BS of the subject from the possible BSs based on the FSoOSCs and the set of probabilities; and determining an action to be performed based on the first identified BS.

24 Claims, 16 Drawing Sheets

(56) References Cited

U.S. PATENT DOCUMENTS

| | | | |
|---|---|---|---|
| 9,095,455 B2* | 8/2015 | Kao | A61F 2/72 |
| 9,195,934 B1 | 11/2015 | Hunt et al. | |
| 9,373,088 B2 | 6/2016 | Nuyujukian et al. | |
| 10,653,330 B2 | 5/2020 | Angle et al. | |
| 2014/0108302 A1 | 4/2014 | Chang et al. | |
| 2014/0257520 A1 | 9/2014 | Kao et al. | |
| 2020/0097081 A1 | 3/2020 | Stone et al. | |
| 2020/0268296 A1 | 8/2020 | Alcaide et al. | |
| 2021/0004085 A1* | 1/2021 | Ketz | G06N 7/005 |

OTHER PUBLICATIONS

Churchland, M. et al., "Cortical Preparatory Activity: Representation of Movement or First Cog in a Dynamical Machine?", in Neuron, vol. 68, issue 4, Nov. 4, 2010, pp. 387-400.

Churchland, M., "Extracting Computational Principles Governing the Relation between Brain Activity and Muscle Activity that are Conserved between Rodents and Primates", NIH Grant 5U19NS104649-04, Sep. 25, 2017, Columbia Univ Health Sciences, available at: https://reporter.nih.gov/project-details/9983208, pp. 1-5.

Henderson, J.M., "Engaging New Cognitive and Motor Signals to Improve Communication Prostheses", NIH Grant 2R01DC014034-06, Stanford University, Apr. 1, 2015, available at: https://reporter.nih.gov/project-details/9886850#patents, pp. 1-5.

Kemere, C. et al., "Detecting Neural-State Transitions using Hidden Markov Modesl for Motor Cortical Prostheses", In Journal of Neurophysiology, vol. 100, No. 4, Oct. 2008, pp. 2441-2452.

Moore, T., "Large-Scale Recordings in Primate Prefrontal Cortex: Mechanisms of Value and Attention", NIH Grant 1R01NS116623-01, Stanford University, Sep. 30, 2020, available at: https://reporter.nih.gov/project-details/9972475#details, pp. 1-5.

Musk, L., "An Integrated Brain-Machine Interface Platform with Thousands of Channels", In the Journal of Medical Internet Resources, vol. 21, No. 10, Oct. 31, 2019, pp. 1-14.

Rao, R.P., "Towards Neural Co-Processors for hte Brain: Combining Decoding and Encoding in Brain-Computer Interfaces", In Current Opinion Nuerobiology, vol. 55, Apr. 2019, pp. 142-151.

Robertson, A., "I Tried the Wristband that lets you Control Computers with your Brain", In The Verge, Jun. 6, 2018, pp. 1-14.

Russo, A.A. et al., "Motor Cortex Embeds Muscle-like Commands in an Untangled Population Response", In Neuron, vol. 97, No. 4, Feb. 21, 2018, pp. 953-966.

Sani, O.G. et al., "Modeling Behavoirally Relevant Neural Dynamis Enablded by Preferential Subspace Identification", In Nature Neuroscience, vol. 24, Nov. 9, 2020, pp. 140-149.

Shanechi, M.M., "Brain-Machine Interfaces from Motor to Mood", In Nature Neuroscience, vol. 22, No. 10, Oct. 2019, pp. 1554-1564.

Stavisky, S.D., "Neural Ensemble Dynamics in Dorsal Motor Cortex during Speech in People with Paralysis", In Elife, vol. 8, Dec. 10, 2019, pp. 1-31.

VA Office of Research and Development, "Restoring High Dimensional Hand Function to Persons with Chronic High Tetraplegia", Clinical Trial NCT03482310, Mar. 29, 2019, available at: https://clinicaltrials.gov/ct2/show/NCT03482310, pp. 1-7.

Visconti, P. et al., "Technical Features and Functionalities of Myo Armband: An Overview on Related Literature and Advanced Applications of Myoelectric Armbands Mainly Focused on Arm Prostheses", in International Journal on Smart Sensing and Intelligent Systems, vol. 8, Jan. 2018, pp. 1-25.

Watanabe, R.N. et al., "Fast Oscillatory Commands from the Motor Cortex can be Decoded by the Spinal Cord for Force Control", In Journal of Neuroscience, vol. 35, No. 40, Oct. 7, 2015, pp. 13687-13697.

International Search Report and Written Opinion dated May 20, 2022 in International Patent Application No. PCT/US2022/014608, pp. 1-14.

* cited by examiner

400

Input:
$S^{ctr}_{n,k}(c, tr, n, k)$ := number of spikes observed from neuron $n$ at time index $k$ of trial $tr$ of action $c$
$A^{ctr}_{m,k}(c, tr, m, k)$ := value of behavioral variable $m$ at time index $k$ of trial $tr$ of action $c$

Output (Neural & Behavioral Trajectories):
$\overline{r}^{ctr}_{n,k}(c, n, k)$ := canonical rate for neuron $n$ at time index $k$ of action $c$
$\overline{a}^{ctr}_{m,k}(c, m, k)$ := canonical behavioral variable $m$ at time index $k$ of action $c$ // Filter single-trial spiking activity into smooth rates.
1  forall *actions c* do
2     forall *trials tr* do
3        forall *neurons n* do
            // Collect spikes into a vector indexed by time.
4           spikes $\leftarrow [S^{ctr}_{n,1}, S^{ctr}_{n,2}, \ldots, S^{ctr}_{n,K_c}]$ where $K_c$ is the number of time indices in action $c$
            // Filter spikes with a Gaussian and store result.
5           rates $\leftarrow$ convolution of spikes with a zero-mean Gaussian kernel
            // These rates can be notated similarly to how individual spike counts were notated.
6           forall *time indices k* do
7              $r^{ctr}_{n,k} \leftarrow$ value of rates at time index $k$
8           end
9        end
10    end
11 end

```
12  // Compute canonical rates and corresponding behavior.
12  forall actions c do
13    forall time indices k do
14      // Average rates across trials.
15      forall neurons n do
16        $\bar{r}_{n,k}^{c,tr}$ ← average value of $r_{n,k}^{c,tr}$ across all trials
17      end
      // Average behavioral variables across trials.
      forall behavioral variables m do
        $\bar{z}_{m,k}^{c,tr}$ ← average value of $z_{m,k}^{c,tr}$ across all trials
      end
    end
21  end
```

Input (Training Data):

$\bar{r}_{n,k}$, $\bar{v}(c, n, k)$ = canonical rate for neuron $n$ at time index $k$ of action $c$ $\bar{z}_{m,k}$, $\bar{v}(c, n, k)$ = canonical behavioral variable $m$ at time index $k$ of action $c$

Output (Parameters):

$\bar{c}_{n,k}$, $\bar{v}(c, n, k)$ = rate index for neuron $n$ at time index $k$ of action $c$ $L$ = lookup table whose $(s, v)$-th entry contains the log-likelihood of observing $s$ spikes in a time bin from a neuron with rate index $v$

Constants:

$\Delta$ := number of time indices pooled into a time bin $\lambda_{min}$ := minimum rate in spikes/time bin $\lambda_{max}$ := maximum rate in spikes/time bin $V$ := constant value determining how rates are sampled between $\lambda_{min}$ and $\lambda_{max}$

FIG. 5A

// Sample rates from $\lambda_{min}$ to $\lambda_{max}$. This allows us to refer to a
// particular rate $\lambda$ using a rate index $v$. This has the benefit of
// memory efficiency ($v$ can be stored as an integer) and allows us to
// use a lookup table with columns indexed by $v$, as described below.
1 forall *rate indices* $v \leftarrow 0$ to $V$ do
2 $\quad \lambda(v) \leftarrow \lambda_{min} + \frac{v}{V}(\lambda_{max} - \lambda_{min})$
3 end

// Learn rate indices for the library of neural trajectories.
forall *actions c* do
  forall *neurons n* do
    forall *time indices k* do
      // Get the mean rate for neuron $n$ over a trailing window at time index $k$ of action $c$.
      $\lambda \leftarrow \frac{1}{\Delta} \sum_{i=0}^{\Delta-1} \bar{r}^c_{n,k-i}$
      // Saturate mean rate so it stays in the range $[\lambda_{min}, \lambda_{max}]$.
      $\lambda \leftarrow \min(\max(\lambda, \lambda_{min}), \lambda_{max})$
      // Convert from rate to rate index.
      $v^c_{n,k} \leftarrow \text{round}\left(\frac{\lambda - \lambda_{min}}{\lambda_{max} - \lambda_{min}} V\right)$
    end
  end
end

FIG. 5C

```
  // Build the lookup table. Note that the computations in this section
  do not depend on the training data collected and could be completed
  prior to even collecting training data.
13 forall possible spike counts s do
14    forall rate indices r do
         // Compute the log-likelihood of observing s spikes in a time bin
         from a neuron with rate λ̃(r) given a Poisson observation model.
15       L(s, r) ← s log λ̃(r) − λ̃(r) − log s!
16    end
17 end
```

Observations:

$s_{n,t} \triangleq \mathcal{V}(n,t) =$ number of spikes observed from neuron $n$ at time $t$

Decoded Variables:

$\hat{z}_{m,t} \triangleq \mathcal{V}(n,t) =$ decoded state of neuron $n$ at time $t$
$\hat{z}_{m,t} \triangleq \mathcal{V}(m,t) =$ decoded behavioral variable $m$ at time $t$

Parameters:

$\overline{r}_{n,k} \triangleq \mathcal{V}(c,n,k) =$ canonical rate for neuron $n$ at time index $k$ of action $c$
$\overline{c}_{n,k} \triangleq \mathcal{V}(c,m,k) =$ canonical behavioral variable $m$ at time index $k$ of action $c$
$c_{n,k}^c \triangleq \mathcal{V}(c,n,k) =$ rate index for neuron $n$ at time index $k$ of action $c$
$L :=$ lookup table whose $(s,v)$-th entry contains the log-likelihood of observing $s$ spikes in a time bin from a neuron with rate index $v$

Constants:

$\Delta =$ number of time indices pooled into a time bin
$\tau' =$ number of previous time bins of spiking activity (in addition to the current time bin) to use in decoding
$\tau = \Delta(\tau' + 1) - 1$

```
// Initialize variables and run decoder.
1 t ← 0
2 $\tilde{q}_{0,k'} \leftarrow 0$ for all $k'$ where $k'$ indexes time bins along neural & behavioral trajectories, i.e., $k' = \frac{k}{\Delta}$ for $k$ that is a multiple of $\Delta$
```

FIG. 6A

```
3  while decoding do
4     t ← t + 1 // time increments
      // Update based on new observations once per time bin.
5     if t is a multiple of Δ then
6        t' = t/Δ
         // Bin spikes.
7        forall neurons n do
8           s̄_{n,t'} = ∑_{i=0}^{Δ-1} s_{n,Δt'-i}
9        end
```

```
10   // Compute log-likelihood of observed spikes given each neural
11      state in the library.
12   forall actions c do
13       q̃_{l,0} ← 0
14       forall time bin indices k' along action c do
15           // Use a recursion to compute log-likelihoods.
16           q̃_{l,k'} ← q̃_{l-1,k'-1}
17           for n ← 1 to total number of neurons do
18               q̃_{l,k'} ← q̃_{l,k'} + L(S̄_{n,l'}, r̄^c_{n,Δk'}) − L(S̄_{n,l'−τ−1}, r̄^c_{n,Δk'−τ−1})
19           end
20       end
21   end
22   // Select the action and time bin index within that action
        corresponding to the most likely neural state.
23   (c, k') ← pair of values (c, k') that maximizes q̃_{l,k'} subject to the constraint k' > τ'
24   end
```

FIG. 6C

```
23  if t > τ then
        // Let estimates reflect time elapsed since the last time bin
           completed.
24      k̂ ← k'Δ + (t − t'Δ)
        // Decode the neural state & behavioral state corresponding to
           the decoded action and time.
25      forall neurons n do
26          f̂_{n,t} ← F̄^c_{n,k̂}
27      end
28      forall behavioral variables m do
29          ẑ_{m,t} ← Z̄^c_{m,k̂}
30      end
31  end
32 end
```

FIG. 6D

SYSTEMS, METHODS, AND MEDIA FOR DECODING OBSERVED SPIKE COUNTS FOR SPIKING CELLS

CROSS REFERENCE TO RELATED APPLICATIONS

This application claims the benefit of U.S. Patent Application No. 63/143,568, filed Jan. 29, 2021, and the benefit of U.S. Patent Application No. 63/210,441, filed Jun. 14, 2021, each of which is hereby incorporated by reference herein in its entirety.

BACKGROUND

Brain-Machine Interfaces (BMIs) have the potential to solve many problems facing humans as well as provide new mechanisms for controlling a wide variety of machines. For example, a BMI can be used to allow a paralyzed human to control a prosthetic device such as an arm, a leg, a hand, a foot, a finger, a toe, etc. Likewise, a BMI can enable monitoring of the brain to detect a state of the brain, such as a seizure state, a resting state, an awake state, etc.

Accordingly, new mechanisms for Brain-Machine Interfaces are desirable.

SUMMARY

In accordance with some embodiments, systems, methods, and media for decoding observed spike counts for spiking cells are provided.

In some embodiments, methods of decoding observed spike counts for spiking cells are provided, the methods comprising: receiving a first set of observed spike counts for the spiking cells; determining a set of probabilities by: retrieving the set of probabilities from stored information; or calculating the set of probabilities based on the stored information, wherein the stored information regards possible biological states of a subject, wherein each of the possible biological states belongs to at least one of a plurality of time sequences of biological states, wherein each of the plurality of time sequences of biological states corresponds to a possible action of the subject, and wherein each probability in the set of probabilities indicates a likelihood of observing a possible spike count for one of the plurality of spiking cells; identifying using a hardware processor a first identified biological state of the subject from the possible biological states based on the first set of observed spike counts and the set of probabilities, wherein the identifying of the first identified biological state of the subject comprises: for each of the possible biological states in each of the plurality of time sequences of biological states: retrieving or calculating a spiking cell probability for each of the spiking cells by matching the first set of observed spike counts to corresponding stored information for the possible biological state; and calculating a combined probability that the first set of spike counts corresponds to the possible biological state based on a combination of the spiking cell probabilities; determining an action to be performed based on the first identified biological state; and causing the action to be performed.

In some of these embodiments, the action is to cause at least a portion of the subject, or a device controlled by the subject, to move relative to space around the subject.

In some of these embodiments, the action is to indicate an internal state of the brain of the subject.

In some of these embodiments, the identifying of the first identified biological state of the subject comprises identifying the first identified biological state based on the first set of observed spike counts, the set of probabilities, and a utility function.

In some of these embodiments, the method further comprises: identifying a second identified biological state of the subject from the possible biological states based on the first set of observed spike counts and the set of probabilities; and determining a third identified biological state from at least the first identified biological state and the second identified biological state.

In some of these embodiments, the spiking cells are muscle cells.

In some of these embodiments, the spiking cells are neurons.

In some of these embodiments, the method further comprises: receiving a subsequent set of observed spike counts for the spiking cells, wherein the subsequent set of observed spike counts are observed at a different time than the first set of observed spike counts are observed; and identifying a subsequent identified biological state of the subject from the possible biological states based on the subsequent set of observed spike counts, the first set of observed spike counts, and the set of probabilities.

In some of these embodiments, the identifying of the first identified biological state of the subject comprises: for each of the possible biological states in each of the plurality of time sequences of biological states: retrieving or calculating a spiking cell probability for each of the spiking cells by matching the first set of observed spike counts to corresponding stored information for the possible biological state; and calculating a combined probability that the first set of spike counts corresponds to the possible biological state based on a combination of the spiking cell probabilities.

In some of these embodiments, the probabilities are log-probabilities.

In some of embodiments, systems for decoding observed spike counts for spiking cells are provided, the systems comprising: a memory; and a hardware processor coupled to the memory and configured to: receive a first set of observed spike counts for the spiking cells; determine a set of probabilities by: retrieving the set of probabilities from stored information; or calculating the set of probabilities based on the stored information, wherein the stored information regards possible biological states of a subject, wherein each of the possible biological states belongs to at least one of a plurality of time sequences of biological states, wherein each of the plurality of time sequences of biological states corresponds to a possible action of the subject, and wherein each probability in the set of probabilities indicates a likelihood of observing a possible spike count for one of the plurality of spiking cells; identify a first identified biological state of the subject from the possible biological states based on the first set of observed spike counts and the set of probabilities, wherein the identifying of the first identified biological state of the subject comprises: for each of the possible biological states in each of the plurality of time sequences of biological states: retrieving or calculating a spiking cell probability for each of the spiking cells by matching the first set of observed spike counts to corresponding stored information for the possible biological state; and calculating a combined probability that the first set of spike counts corresponds to the possible biological state based on a combination of the spiking cell probabilities;

determine an action to be performed based on the first identified biological state; and cause the action to be performed.

In some of these embodiments, the action is to cause at least a portion of the subject, or a device controlled by the subject, to move relative to space around the subject.

In some of these embodiments, the action is to indicate an internal state of the brain of the subject.

In some of these embodiments, the identifying of the of first identified biological state of the subject comprises identifying the first identified biological state based on the first set of observed spike counts, the set of probabilities, and a utility function.

In some of these embodiments, the hardware processor is further configured to: identify a second identified biological state of the subject from the possible biological states based on the first set of observed spike counts and the set of probabilities; and determine a third identified biological state from at least the first identified biological state and the second identified biological state.

In some of these embodiments, the spiking cells are muscle cells.

In some of these embodiments, the spiking cells are neurons.

In some of these embodiments, the hardware processor is further configured to: receive a subsequent set of observed spike counts for the spiking cells, wherein the subsequent set of observed spike counts are observed at a different time than the first set of observed spike counts are observed; and identify a subsequent identified biological state of the subject from the possible biological states based on the subsequent set of observed spike counts, the first set of observed spike counts, and the set of probabilities.

In some of these embodiments, the identifying of the first identified biological state of the subject comprises: for each of the possible biological states in each of the plurality of time sequences of biological states: retrieving or calculating a spiking cell probability for each of the spiking cells by matching the first set of observed spike counts to corresponding stored information for the possible biological state; and calculating a combined probability that the first set of spike counts corresponds to the possible biological state based on a combination of the spiking cell probabilities.

In some of these embodiments, the probabilities are log-probabilities.

In some of embodiments, non-transitory computer-readable medium containing computer executable instructions that, when executed by a processor, cause the processor to perform a method of decoding observed spike counts for spiking cells are provided, the method comprising: receiving a first set of observed spike counts for the spiking cells; determining a set of probabilities by: retrieving the set of probabilities from stored information; or calculating the set of probabilities based on the stored information, wherein the stored information regards possible biological states of a subject, wherein each of the possible biological states belongs to at least one of a plurality of time sequences of biological states, wherein each of the plurality of time sequences of biological states corresponds to a possible action of the subject, and wherein each probability in the set of probabilities indicates a likelihood of observing a possible spike count for one of the plurality of spiking cells; identifying a first identified biological state of the subject from the possible biological states based on the first set of observed spike counts and the set of probabilities, wherein the identifying of the first identified biological state of the subject comprises: for each of the possible biological states in each of the plurality of time sequences of biological states: retrieving or calculating a spiking cell probability for each of the spiking cells by matching the first set of observed spike counts to corresponding stored information for the possible biological state; and calculating a combined probability that the first set of spike counts corresponds to the possible biological state based on a combination of the spiking cell probabilities; determining an action to be performed based on the first identified biological state; and causing the action to be performed.

In some of these embodiments, the action is to cause at least a portion of the subject, or a device controlled by the subject, to move relative to space around the subject.

In some of these embodiments, the action is to indicate an internal state of the brain of the subject.

In some of these embodiments, the identifying of the first identified biological state of the subject comprises identifying the first identified biological state based on the first set of observed spike counts, the set of probabilities, and a utility function.

In some of these embodiments, the method further comprises: identifying a second identified biological state of the subject from the possible biological states based on the first set of observed spike counts and the set of probabilities; and determining a third identified biological state from at least the first identified biological state and the second identified biological state.

In some of these embodiments, the spiking cells are muscle cells.

In some of these embodiments, the spiking cells are neurons.

In some of these embodiments, the method further comprises: receiving a subsequent set of observed spike counts for the spiking cells, wherein the subsequent set of observed spike counts are observed at a different time than the first set of observed spike counts are observed; and identifying a subsequent identified biological state of the subject from the possible biological states based on the subsequent set of observed spike counts, the first set of observed spike counts, and the set of probabilities.

In some of these embodiments, the identifying of the first identified biological state of the subject comprises: for each of the possible biological states in each of the plurality of time sequences of biological states: retrieving or calculating a spiking cell probability for each of the spiking cells by matching the first set of observed spike counts to corresponding stored information for the possible biological state; and calculating a combined probability that the first set of spike counts corresponds to the possible biological state based on a combination of the spiking cell probabilities.

In some of these embodiments, the probabilities are log-probabilities.

BRIEF DESCRIPTION OF THE DRAWINGS

FIGS. 4A-4B is an example of pseudocode for a first stage of a training process in accordance with some embodiments.

FIGS. 5A-5D is an example of pseudocode for a second stage of a training process in accordance with some embodiments.

FIGS. 6A-6D is an example of pseudocode for a decoding process in accordance with some embodiments.

DETAILED DESCRIPTION

Figure 1:
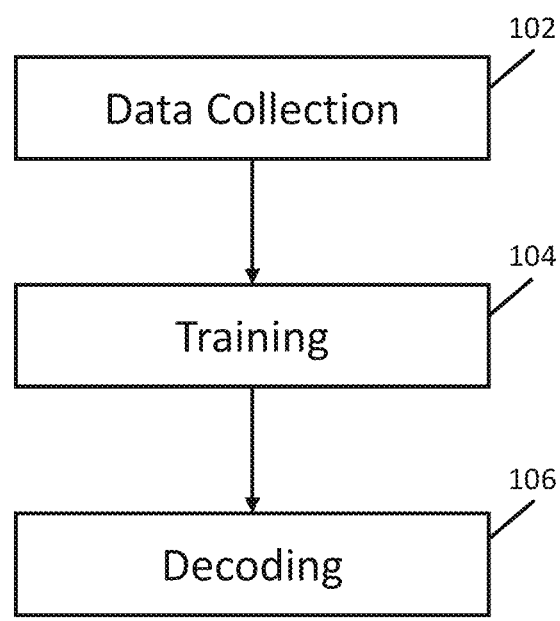
FIG. 1 is an example of a high-level process for a Brain-Machine Interface (BMI) in accordance with some embodiments.

In accordance with some embodiments, mechanisms (which can include systems, methods, and media) for Brain-Machine Interfaces (BMIs) are provided. As used herein, a "Brain-Machine Interface" or BMI is a device that can interface with a nervous system (which can include the brain, the spinal cord, and peripheral nerves) and/or with muscles in order to translate neural information into one or more signals to be subsequently used for controlling an external device, monitoring the state of the brain, visualizing neural activity, and/or for any other suitable purpose. These mechanisms can be used with human subjects and/or any other suitable animal subjects, in some embodiments.

In some embodiments of these mechanisms, the spiking (action potential) activity of neurons of a subject is observed and used to learn patterns in that spiking activity that correspond to certain states of the brain (e.g., epileptic events, attention, decision states, etc.) and/or intended actions (e.g., move head, move mouth, move arm, move leg, move hand, move foot, move finger, move toe, stimulate muscles, control cursor, control handwriting instrument, control speech synthesizer, start/stop wheel chair, turn wheel chair, etc.). This can be referred to herein as training. Upon observing subsequent spiking activity in the neurons of the subject when not training, that subsequent spiking activity can be compared to the learned patterns and used to indicate that the brain, nervous system, muscles, or any subset of these, is in a particular state and/or to cause a corresponding intended action to occur via any suitable mechanism (e.g., such as a prosthetic limb, wheelchair, computer cursor, robotic device, etc.) in some embodiments. This can be referred to herein as decoding.

In some embodiments, a "neuron" as described herein may actually be the combined response of a small number of nearby neurons. Thus, when a "neuron" is referred to herein, the neuron should be whatever is the source of spiking activity that is detected by a single electrode or sensor being used to make observations.

In some embodiments, the spiking activity of one or more neurons can be inferred indirectly from other measurements. For example, in some embodiments, electrical activity measured from one or more muscles can be observed and, based on that electrical activity, spiking activity of motor neurons in the spinal cord can be inferred.

In some embodiments of these mechanisms, decoding can be performed in real time. In some embodiments, decoding can be performed in non-real-time.

In some embodiments of these mechanisms, the mechanisms may use a model of neural activity in a multi-dimensional state space in which each dimension represents the firing rate of a neuron being observed. Neural activity at any given time corresponds to a single location in this state space (the "neural state"), in some embodiments. This model is generated during a training phase in some embodiments. In some embodiments, training can be performed prior to any decoding (i.e., offline training) and/or be performed during decoding (i.e., online training). In this model, the "firing rate" of a neuron at a given time is a numerical value related to how many spikes the neuron is likely to emit in a brief window of time. Spiking is probabilistic (higher rates tend to predict more spikes, but not with certainty), but the firing rate dictates (via a probabilistic model of spiking) the probabilities associated with observing zero spikes per unit time, one spike per unit time, etc. A consequence of the stochasticity in spiking is that the firing rate of a neuron may not be accurately approximated from its spiking activity at any given moment, in some embodiments. Nevertheless, the time-varying rates of every neuron can be accurately approximated by collecting many "trials" of a repeated action, filtering spike counts across time for each neuron within each trial, and then averaging those filtered spike counts across trials, in some embodiments. In some embodiments, we refer to an approximated firing rate of a neuron at a particular time point within the execution of a particular action as a "canonical rate". The pattern of canonical rates over time (corresponding to a pattern of neural states over time) for a particular action yields a "neural trajectory" that is presumed to be present on each and every trial of that action, and is presumed to determine (probabilistically) the pattern of spiking that will be observed when a subject thinks of performing the action.

In some embodiments, each neural trajectory corresponds to a particular action, for which there are corresponding behavioral variables that change over time throughout the execution of the action. In some embodiments, the collection of behavioral variables at a single moment in time is referred to as a "behavioral state" and the pattern of behavioral states over time corresponding to a particular action (and therefore a particular neural trajectory) is referred to as a "behavioral trajectory".

In some embodiments, neural trajectories and corresponding behavioral trajectories may be learned using an approach that takes as an input neural trajectories and corresponding behavioral trajectories previously learned from the same subject or previously learned from one or more other subjects. In this approach, in some embodiments, a process may receive previously generated neural trajectories and corresponding behavioral trajectories along with recently collected neural and/or behavioral data from one or more trials of one or more actions from a subject, and learns a transformation of the previously generated neural trajectories and corresponding behavioral trajectories in order to perform training and decoding in a BMI as described herein.

In some embodiments, each action (e.g., moving an arm in a certain way, moving a leg in a certain way, etc.) can have its own neural trajectory through the multi-dimensional state space. Together, these can be used to form a library of neural trajectories. This library, while containing some possible states, does not contain all possible states. In some embodiments, this library, while containing possible neural trajectories, does not contain all possible neural trajectories (each neural trajectory being a sequence of neural states). Thus, in some embodiments, decoding can make an assumption that the true neural state, at any given time, will always be somewhere along one of the neural trajectories. That is, although a neural state is not necessarily constrained to a low-dimensional subspace, it can be assumed to be massively constrained regarding where it can be within a high-dimensional space. In some embodiments decoding can make the assumption that the true neural state lies in the local neighborhood of two or more candidate neural states from the library. In some embodiments, there exists a corresponding library of behavioral trajectories, with a oneto-one correspondence with the neural trajectories, such that if a neural state is known a corresponding behavioral state can be determined.

In some embodiments, given an observed set of spike counts for a set of observed neurons at a current point in time, every neural state from the library (i.e., every neural state along each of these neural trajectories) can be assigned a probability that it corresponds to the current state. These probabilities can then be used to rapidly perform maximum a posteriori estimation to determine the neural state along the neural trajectories that has the highest probability of corresponding to the current state in some embodiments. Considering only those neural states along the neural trajectories as possibilities for the current state is far more efficient than considering all neural states in the vast state space, in some embodiments. In some embodiments, every neural state from the library corresponds to a particular time during a particular action.

Once the most probable neural state has been determined, the most probable behavioral state at that time can be determined, in some embodiments. In some embodiments, each neural state corresponds to a moment in a specific neural trajectory, within the library of neural trajectories. Because of the one-to-one correspondence between the neural and behavioral libraries in some embodiments, this corresponds to a moment in a specific behavioral trajectory. Thus, in some embodiments, an estimate of the neural state can lead directly to an estimate of the behavioral state. In embodiments where the neural state is assumed to lie in the local neighborhood of two or more candidate neural states from the neural library, the behavioral state may be similarly assumed to lie in the local neighborhood of the corresponding states from the behavioral library. In some embodiments, other techniques for associating behavioral states with neural states along the learned neural trajectories can be used. For example, in some embodiments, a linear regression between the neural trajectories and the behavioral variables in the training data can be used to learn which behavioral states to associate with neural states.

In some embodiments, the estimated neural state (or a set of candidate states) is based on the likelihood of the empirically observed spikes, across neurons, for each neural state in the library, which can be computed because the neural state specifies the likelihood of the spike-count observed for each and every neuron. In some embodiments, the neural state is expressed in terms of a "firing rate" and a spike-count likelihood for each neuron can be computed via a Poisson model of spiking. In some embodiments, for each neuron and every neural state in the library, the likelihood of all plausible spike counts (0 spikes, 1 spike, 2 spikes, etc.) may be precomputed and stored in a look-up table. In some embodiments these may be rapidly computed online.

In some embodiments, the likelihood of all observed spikes (across all neurons), for a given neural state, can factorize into a product of neuron-specific likelihoods allowing the overall likelihood to be computed by multiplying neuron-specific likelihoods. In some embodiments, these computations may be simplified and made more robust by using log-likelihoods, allowing the overall log-likelihood to be computed as the sum of neuron-specific log-likelihoods.

Although the number of possible spike count configurations (across neurons and across times) can be massive (even for a library with a small number of neural states), by breaking the overall likelihoods (or log-likelihoods) down into neuron-specific likelihoods (or log-likelihoods) that can be rapidly computed or retrieved from one or more lookup tables, decoding can rapidly compute the overall likelihoods or log-likelihoods associated with each neural state by combining neuron-specific likelihoods or log-likelihoods using multiplication or addition, respectively, in some embodiments. In some embodiments, the combination of a library of neural states and the factorization of likelihoods avoids the time-consuming computation (or memory-intensive storage) of likelihoods across a vast number of possible temporal spike patterns and a vast number of possible neural states.

In some embodiments, recursion can be used to compute likelihoods (or log-likelihoods) by re-using many of the computations performed by the decoding process when generating the neural state estimate at one or more prior moments. This recursion further reduces the number of operations required during decoding, which speeds up execution time considerably, in some embodiments.

Turning to FIG. 1, a flow diagram of an example process 100 for a brain-machine interface in accordance with some embodiments is shown. As illustrated, at 102, process 100 begins by performing a data collection process.

In some embodiments of this process, a subject is connected to a system for detecting and storing neural activity from a collection of neurons. Any suitable system can be used in some embodiments and neural activity can be detected and stored from any suitable number of neurons in some embodiments. Further features of hardware that can be used for detecting and storing neural activity are described below in connection with FIGS. 7-9.

In some embodiments, during detecting and storing, the subject performs (if healthy) or imagines performing (if paralyzed) each possible action that one wishes to be able to decode a fixed number of times (each repeated occurrence of the action is referred to as a "trial"). Data (including neural spike times and behavioral data (which can be simulated in some embodiments)) is then detected and stored in any suitable manner. In some embodiments, any suitable technique for filtering and thresholding neural activity to detect spikes may be performed while detecting and storing neural activity.

Next, at 104, the neural activity and behavioral data are processed in a training process that generates the parameters necessary for decoding, including the library of neural trajectories. Any suitable processing in any suitable training procedure that generates the parameters necessary for decoding can be used in some embodiments. For example, a training procedure that generates the parameters necessary for real-time decoding can be used in some embodiments. In some embodiments, this may be done as described below in connection with FIGS. 4A-4B and 5A-5D.

Then, at 106, a decoding process can be performed. During decoding, a stream of spiking activity from a subject can be received and estimates of the neural state and the behavioral state can be determined. The behavioral state is a vector of behavioral variables (such as position, velocity, movement goal, etc.) and one or more additional computations may be performed on those variables (e.g., smoothing over time) before sending them to an external device capable of enacting an action (e.g., a prosthetic arm). In some embodiments, decoding can be performed in real time. In some embodiments, decoding can be performed in non-real time. In some embodiments, this may be done as described below in connection with FIGS. 6A-6D.

Figure 2:
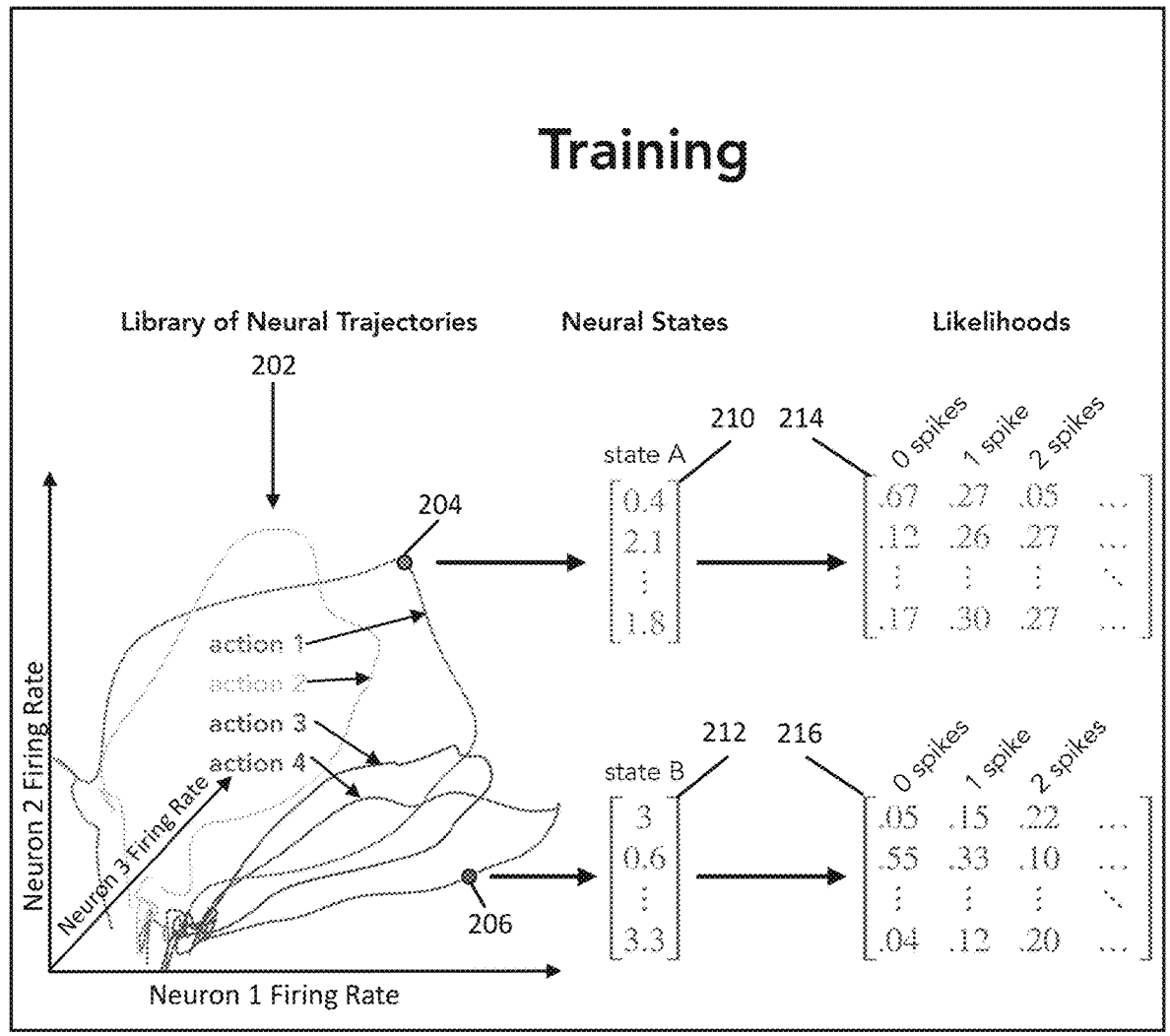
FIG. 2 is an example of an illustration of a training process in accordance with some embodiments.

Turning to FIG. 2, an illustration of a training process in accordance with some embodiments is shown.

In the left third of FIG. 2, a library of neural trajectories 202 are illustrated in accordance with some embodiments. The neural trajectories represent the canonical rates (in units of spike counts per unit time) of all observed neurons over time. One trajectory is shown for each of four actions. Thus, if there are 128 measured neurons, the neural trajectories can be represented in a 128-dimensional space. For the purposes of illustration and clarity, the neural trajectories shown in FIG. 2 are only shown in a three-dimensional space (i.e., three neuron activity dimensions). Note that, in the full 128-dimensional space, the total number of possible neural states is extremely large; even if each neuron's rate is divided into only $10^{1280}$, there are $10^{128}$ total possible neural states. The number of possible neural trajectories is larger still. For example, if considering neural trajectories that span 10 time-steps, there are $10^{1280}$, far larger than the number of atoms in the observable universe. Thus, checking how likely a particular pattern of spikes is for all possible neural trajectories would be computationally intractable on real machines. In contrast, the library of neural trajectories will be much smaller: for 100 actions and 100 time-points on each action, there would be only 10,000 states to consider. Thus, even if it were necessary to consider many more actions or time-points, computation of the likelihood of the spikes given every neural state would remain tractable.

Neural activity at a single moment in time can be summarized by a neural state. For example, points 204 and 206 (each representing a moment during a different action) correspond to neural states 210 and 212, respectively. The values in the state vectors 210 and 212 are the average number of spikes expected within a fixed time window (e.g., 20 milliseconds) for each neuron (each a row in the state vectors) for the corresponding point in time for that action. For example, the second neuron would be expected to produce 2.1 spikes (on average) at moment 204, which might be 200 ms after the beginning of a rightwards reach. This same second neuron would be expected to produce 0.6 spikes (on average) at moment 206, which might be 150 ms after the beginning of a downwards reach. (Note that a neuron always produces a small whole number of spikes, e.g.: 0, 1, 2, 3, etc. However, a neuron may still produce 0.6 spikes per time bin on average, much like a coin can only yield heads a whole number of times when repeatedly flipped, yet may yield heads at a rate of 0.5 heads per flip on average).

The right third of FIG. 2 shows example likelihood matrices 214 and 216 representing neuron-specific likelihoods of detecting given spike counts (in the columns) from neurons (in the rows) at the corresponding point in time for given actions corresponding to points 204 and 206, respectively. These neuron-specific likelihoods are calculated (as described further below) based on a Poisson model of spiking that takes canonical rates from the neural states along the neural trajectories in the library as parameters. For example, the top row of matrix 214 shows a likelihood of 0.67 (i.e., 67%) of detecting zero spikes from neuron 1, a 0.27 likelihood of detecting one spike from neuron 1, and a 0.05 likelihood of detecting two spikes from neuron 1 within a fixed time window at the corresponding point in time for action 1.

Figure 3:
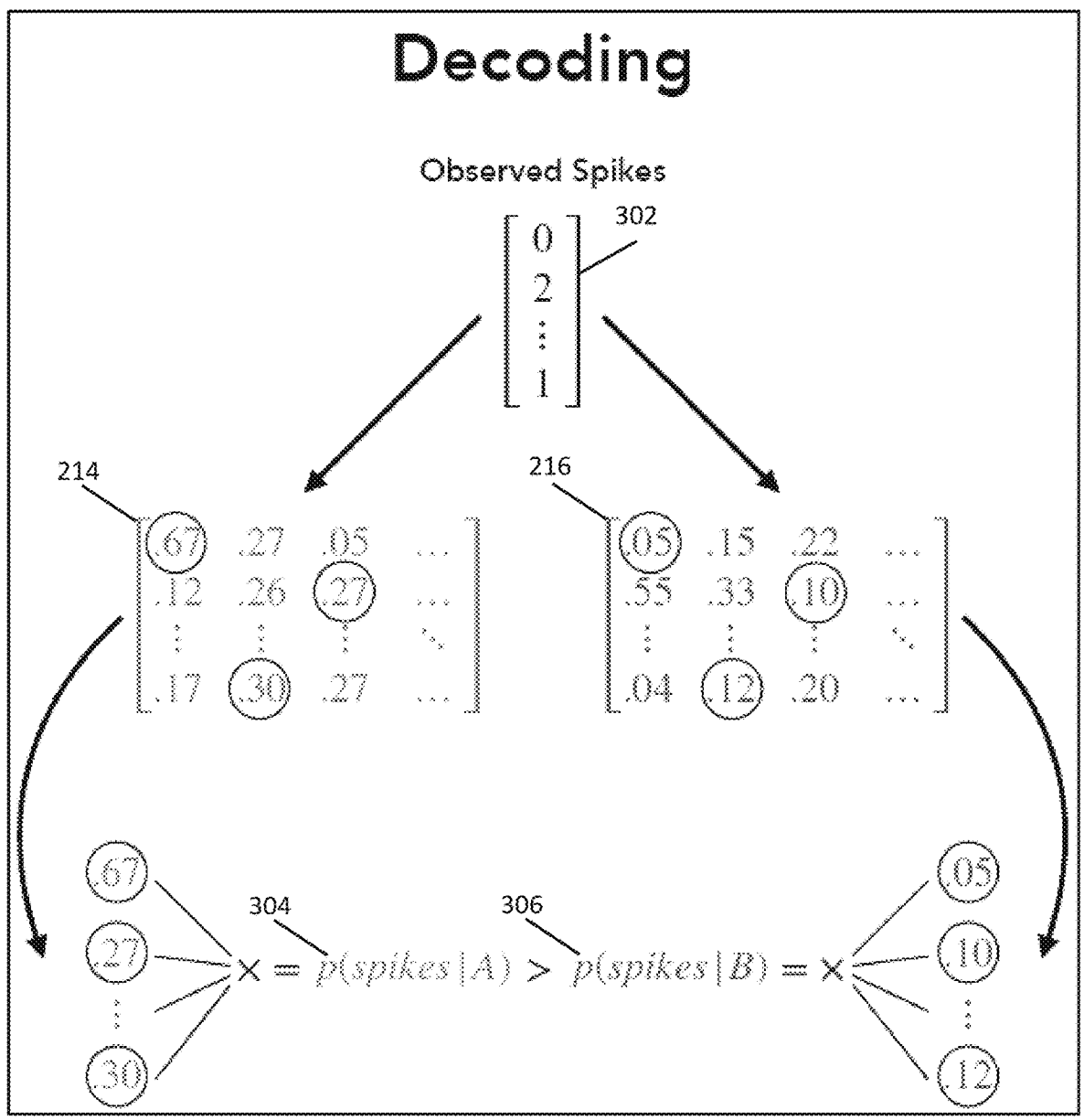
FIG. 3 is an example of an illustration of a decoding process in accordance with some embodiments.

Turning to FIG. 3, an illustration of a decoding process in accordance with some embodiments is shown.

As illustrated, an observed spike count vector 302 is received by the decoding process. Any suitable spike counts can be received from any suitable device in any suitable manner in some embodiments. In some embodiments, the spike counts can be received from the same equipment and installation of that equipment as was used during training to ensure a correspondence between neuron numbers during training and decoding.

Next, the observed spike counts are used to determine probabilities associated with each neural state in the library based on likelihood matrices generated during training. For example, as shown in vector 302, spike counts of zero, two, and one were observed for the first neuron, the second neuron, and the last neuron, respectively. These spike counts can then be used to index likelihood matrices 214 and 216 (as well as others based on the number of actions trained and the number of time indices along the neural trajectories for those actions). So, continuing the example, a spike count of zero for the first neuron can be used to select a neuron-specific likelihood of 0.67 from matrix 214 and a neuron-specific likelihood of 0.05 from matrix 216. Likewise, a spike count of two for the second neuron can be used to select a neuron-specific likelihood of 0.27 from matrix 214 and a neuron-specific likelihood of 0.10 from matrix 216. Neuron-specific likelihoods associated with the observed spike counts from other neurons can similarly be determined. Finally, a spike count of one for the last neuron can be used to select a neuron-specific likelihood of 0.30 from matrix 214 and a neuron-specific likelihood of 0.12 from matrix 216.

These neuron-specific likelihoods can then be combined (e.g., by multiplying them for likelihoods and by summing them for log-likelihoods) to determine overall likelihoods (e.g., likelihoods 304 and 306) for the observed spikes given neural states in the library. These likelihoods can be directly compared (as shown in FIG. 3) using maximum likelihood estimation to select a likely neural state. Additionally or alternatively, these likelihoods can be combined with prior beliefs (using Bayes' theorem) about how common or rare certain neural states are in order to compute probabilities for each neural state and subsequently perform maximum a posteriori estimation of the most probable neural state in some embodiments. In some embodiments, the prior probabilities will be equal for all neural states in the library such that the maximum likelihood approach illustrated in FIG. 3 will yield the same estimated neural states as the aforementioned maximum a posteriori approach.

As shown in connection with FIGS. 2 and 3, in some embodiments, the decoding method assumes that the neural state will always be somewhere along one of the neural trajectories in the library. This assumption enables one to precompute the neuron-specific likelihoods of observing any possible spike count from any neuron while anywhere along one of these neural trajectories and store these neuron-specific likelihoods in lookup tables in memory in some embodiments. Decoding the correct neural state then simply amounts to querying these lookup tables according to real-time spiking observations, combining the queried neuron-specific likelihoods into overall likelihoods of the observed spikes, and determining which neural state is the most probable in some embodiments. Although FIGS. 2 and 3 only illustrate lookup tables for two neural states (i.e., neural states 210 and 212), in some embodiments, a lookup table can be generated for every neural state (that is, every time point along every action). Thus, for example, if there are 20 actions and 100 time points along each action, 2000 lookup tables could be created in some embodiments. In some embodiments, any two or more lookup tables can be combined into a single lookup table. In some embodiments, a more memory-efficient approach to utilizing lookup tables is employed in which a lookup table is generated with entries for each possible spike count and each of a finite set of rates. This latter approach is described in FIGS. 5A-5D.

Noting that the neural state evolves over time in a predictable way allows historical spiking observations to further improve this estimation in some embodiments. For example, in some embodiments, the likelihoods determined in FIG. 3 for a time interval (time bin) can be combined with the likelihoods from the same neural trajectories for a given number of immediately previous time intervals (time bins) in a sliding window being considered. In some embodiments, each time interval (time bin) can correspond to 20 ms (or any other suitable value; e.g., anywhere between 1 and 100 ms) and the sliding window can correspond to 400 ms (or any other suitable value; e.g., anywhere between the size of the time interval and 2 s).

In some embodiments, the estimated neural state will correspond to a particular action and a particular time point within the execution of that action. Thus, the appropriate behavior can be decoded by simply rendering the behavioral variables from the training data that correspond to the estimated action at the estimated time point, in some embodiments. In some embodiments, the neural state will lie in the local neighborhood of two or more candidate neural states from the library, each of which corresponds to a particular action and a particular time point within the execution of that action. In some embodiments, the appropriate behavior can be decoded by rendering behavioral variables in the local neighborhood of two or more behavioral states that correspond to candidate neural states.

In the illustration of FIGS. 2 and 3, only two neural states are being checked. However, in practice, the observed spikes are compared to the likelihood matrices for all actions and time points within those actions (where these time points actually correspond to time intervals), in some embodiments.

Further details of the mechanisms described herein in accordance with some embodiments are now provided.

The decoder can begin by receiving measured spiking activity from N neurons at time sample t in some embodiments. This received measured spiking activity can be designated as $s_t \in S^N$ where $S = \{0, 1, \ldots, S\}$, in some embodiments. Spikes in the observed spiking activity are associated with some underlying neural state $x_t \in \mathbb{R}^N$ and a corresponding behavioral state $z_t \in \mathbb{R}^M$ where M is the number of behavioral variables (e.g., x- and y-velocity of the hand).

Next, spiking activity can be binned in time such that $$\bar{s}_{i'} = \sum_{i=0}^{\Delta-1} s_{\Delta i' - i},$$

in some embodiments. The spiking activity can be binned in time in any suitable manner and over any suitable time period. For example, each bin can be 20 ms (or any other suitable value) wide in time.

Given recent spiking history $\bar{s}_{t'-\tau':t'}$ (spike counts from the most recently completed bin $t' = \lfloor t/\Delta \rfloor$ and $\tau'$ previous bins), posterior distributions over neural states $P(x_t|\bar{s}_{t'-\tau':t'})$ and over behavioral states $P(z_t|\bar{s}_{t'-\tau':t'})$ can be inferred, in some embodiments. Maximum a posteriori estimation can then be performed, in some embodiments, to generate estimates for both the neural state and the behavioral state.

In accordance with some embodiments, a model of the following form can be used:

$$x_t \sim \text{Unif}(\Omega)$$

$$x_{t-i-1} = g(x_{t-i}), i \in \{0, 1, \ldots, \tau-1\}$$

$$\bar{s}_{t'-i'} \sim \text{Pois}\left(\frac{1}{\Delta}\sum_{i=0}^{\Delta-1} x_{\Delta(t'-i')-i}\right), i' \in \{0, 1, \ldots, \tau'\}$$

$$z_t = f(x_t)$$

where $g: \Omega^+ \to \Omega^+$ is a deterministic state-transition function, $f: \Omega \to \Phi$ is an output function, $\delta = t - \Delta t'$ is the number of samples elapsed since the last time bin completed, and $\tau = \delta + \Delta(\tau'+1) - 1$ indicates the extent of the deterministic history for $x_t$ (matching the extent of recent spiking history). In some embodiments, the set $\Omega^+$ and a subset $\Omega \subset \Omega^+$ can be constructed by assuming that for each of C actions there is a finite, ordered set of neural states (a neural trajectory), notated by $$\omega_c = \{\bar{x}_1^c, \bar{x}_2^c, \ldots, \bar{x}_{K_c}^c\} \quad (5)$$

where $\bar{x}_k^c \in \mathbb{R}^N$ is the c-th neural trajectory. In some embodiments, the following can then be defined: $\Omega^+ = \cup_c \omega_c$, $\Omega = \{\bar{x}_k^c \in \Omega^+ | k > \tau\}$, $g(\bar{x}_k^c) = \bar{x}_{k-1}^c$ for $k > 1$. In some embodiments, the set $\Omega^+$ is referred to as a library of neural trajectories.

In some embodiments, other models of spiking can be used to compute neuron-specific likelihoods. More particularly, for example, in some embodiments, a binomial distribution may be used to compute the likelihood that a spike occurs or does not occur from each neuron in a fixed window of time for a given neural state. In some embodiments, the likelihoods of spike-counts can be directly estimated from the frequencies with which they are observed in data. In some embodiments, the likelihood that a particular neuron spikes at any given time may be determined by the rate of that neuron, the rate of other neurons, and/or the spiking activity observed from other neurons.

In some embodiments, $x_t$, referred to as a neural state herein, may be any "biological state" that determines the likelihood of observing spike counts for each neuron. More particularly, for example, in some embodiments, a biological state that corresponds to the activity of muscles and determines the likelihood of observing all possible spike counts from each neuron may be used in connection with the decoding methods described herein.

In some embodiments, the only parameters to be learned from data are the elements of $\Omega^+$ and the mapping $f$. Given any particular present state, in some embodiments, an assumption is made of a deterministic recent past to which recent spiking observations can be compared. This assumption reflects that neural activity generally obeys stereotyped patterns across neurons and recent time for any particular condition ("condition" is synonymous with "action" herein), in some embodiments.

Neural activity can be modelled as sparse, treating $\Omega$ as a finite set. Visualized in a state space, the elements of $\Omega$ resemble a "mesh" of neural states. Conceptually, it is useful to think of this mesh as a discrete approximation to a continuous d-manifold where d may be quite low, but the linear dimensionality of the manifold may be quite high. The behaviors related to $\Omega$ via $f$ are fundamentally continuous in time and may vary on a continuum across conditions (e.g., subject's arm reaches in any direction) in some embodiments. Yet, in some embodiments, these forms of variation might still only yield d=2, suggesting a highly sparse model of neural states may be appropriate. The approach described herein can accommodate this form of local continuity in two ways, in some embodiments. First, the mesh can become very fine, approximating a continuous manifold of neural states, by modeling neural trajectories finely in time and choosing a large C with many neural trajectories corresponding to a spectrum of similar behaviors, in some embodiments. Second, the mesh can be coarse and interpolation can be used to consider states not explicitly defined in Ω or Φ, in some embodiments.

In some embodiments, in accordance with the observation model in (3), the average neural state over A samples should correspond to a vector of expected spike counts for each neuron over that time window. Thus, one could learn $\Omega^+$ by collecting repeated trials for each of C conditions and let the vector $\overline{x}_k^c$ be the average number of spikes observed in condition c at time k for each neuron, normalized to units of spikes per bin. However, directly averaging spiking activity at a high sampling rate can yield noisy rate estimates. Thus, an assumption of smoothness can be incorporated in the neural state by first convolving each spike time-series with a kernel (e.g., boxcar or Gaussian) prior to averaging, in some embodiments.

In some embodiments, neural trajectories can be learned via other methods. For example, in some embodiments neural trajectories may be learned via a variational autoencoder. More particularly, for example, in some embodiments, this can be accomplished by using the method LFADS (Latent Factor Analysis via Dynamical Systems). As another example, in some embodiments, neural trajectories may be learned from filtering the spiking activity on individual trials. More particularly, for example, in some embodiments, this can be accomplished by allowing every instance of an action observed during training to define its own neural trajectory.

In some embodiments, dimensionality reduction techniques may be used to reduce the dimensionality of the neural trajectories across neurons or across actions. For example, in some embodiments, this can be accomplished by 1) using one of the aforementioned techniques for learning a set of neural trajectories, 2) concatenating the rates in those neural trajectories into a large matrix where rows index either neurons or actions, 3) using principal components analysis to reduce the row rank of the matrix, and 4) dividing the matrix back up into neural trajectories (i.e., undoing the concatenation).

In some embodiments, each neural state in Ω corresponds to a particular condition and a particular time within that condition, for which there is corresponding behavioral data. Let the vector $\overline{z}_k^c \in \Phi$ be the trial-averaged behavioral state for condition c at time k where k>τ. In some embodiments, this affords the opportunity to introduce a straightforward condition-specific mapping between the neural state and behavior: $f(\overline{x}_k^c) = \overline{z}_k^c$. In some embodiments, it can be assumed that $\overline{z}_{k_1}^{c_1} = \overline{z}_{k_2}^{c_2}$ if and only if $c_1 = c_2$ and $k_1 = k_2$, and $\overline{x}_{k_1}^{c_1} = \overline{x}_{k_2}^{c_2}$ if and only if $c_1 = c_2$ and $k_1 = k_2$. In some embodiments, this can be made trivially true, e.g., by letting c and k be the first two behavioral variables in the behavioral state. Thus, $f$ is invertible in some embodiments.

In some embodiments, the prior in (1) ensures that $P(x_t=x|\overline{s}_{t'-\tau':t'})=0$ if $x \notin \Omega$. Every element of Ω can be written as $\overline{x}_k^c$ for some c and k. Thus, the posterior probabilities over neural states in Ω can be written as:

$$P(x_t = \overline{x}_k^c | \overline{s}_{t'-\tau':t'}) \propto \sum_{i'=0}^{\tau'} \sum_{n=1}^{N} h(\overline{s}_{n,t'-i'}, \lambda_{n,k-\delta-\Delta i'}^c)$$

$$\lambda_{n,j}^c = \frac{1}{\Delta} \sum_{i=0}^{\Delta-1} \overline{x}_{n,j-i}^c$$

where $h(s,\lambda) = \lambda^s e^{-\lambda}/s!$, $\overline{s}_{n,i}$, and $\overline{x}_{n,i}^c$ are the n-th components of $\overline{s}_{i'}$, and $\overline{x}_i^c$, respectively. Recall that δ is the number of time samples elapsed since the completion of the most recent time bin. A normalizing constant can convert (6) into full posterior probabilities. Computing this constant is straightforward because Ω is finite. The posterior over behavioral states can be written in terms of the posterior over neural states. $P(z_t=z|\overline{s}_{t'-\tau':t'})=0$ if $z \notin \Phi$, but for behavioral states in Φ the posterior probabilities are:

$$P(z\overline{z}_k^c | \overline{s}_{t'-\tau':t'}) = P(x_t = f^{-1}(\overline{z}_k^c) | \overline{s}_{t'-\tau':t'})$$

In some embodiments, maximum a posteriori estimation can be performed on the log-transformed neural state posterior and the behavioral estimate can be read out directly as follows:

$$\hat{x}_t = \underset{x_k^c \in \Omega}{\mathrm{argmax}} \sum_{i'=0}^{\tau'} \sum_{n=1}^{N} \log h(\overline{s}_{n,t'-i'}, \lambda_{n,k-\delta-\Delta i'}^c)$$

$$\hat{z}_t = f(\hat{x}_t)$$

In some embodiments, maximum a posteriori estimation can be performed on the neural state posterior directly (rather than the log-transformed neural state posterior) and the behavioral estimate can be read out directly. In some embodiments, the decoded neural state might be a function of the log-likelihoods other than argmax( ). In some embodiments, the decoded neural state might be chosen to maximize a utility function based both on the log-likelihoods and the cost-benefit of each decodable neural state and corresponding behavioral state. More particularly, for example, a utility function may assign greater cost to states or trajectories that are potentially unsafe (e.g., a wheelchair erroneously transitioning from 'stopped' to 'moving' may pose a greater hazard to the safety of a subject than a wheelchair erroneously transitioning from 'moving fast' to 'moving slow'), in some embodiments. In some embodiments, a neural network can be used to approximate the training procedure or the decoding procedure described herein. More particularly, for example, a neural network may be used to approximate (9) and/or (10) in some embodiments. In some embodiments, likelihoods could be computed for a subset of plausibly high-likelihood neural states identified via some heuristic measure (i.e., likelihoods need not be precisely estimated for neural states that would result in very low likelihoods, as decoding may not be based on such neural states in some embodiments).

In some embodiments, one can proceed with querying (9) for all $\overline{x}_k^c \in \Omega$, selecting the most probable neural state, then reading out the associated behavioral state with (10).

Additionally or alternatively, if one wishes to speed up this process, e.g., to deploy in a real-time application, a method for approximating (9) with a considerably reduced computational burden can be used as described below.

Notice that the log-likelihood term in (9) only varies as a function of spike count and rate. Spike counts are finite and firing rates have limited dynamic ranges, which can be discretized, so it is possible to precompute and store these log-likelihoods in a lookup table in memory. Suppose the dynamic range of rates is given by $[\lambda_{min}, \lambda_{max}]$ and this range is sampled with V+1 values such that $$\bar{\lambda}(v) = \lambda_{min} + \frac{v}{V}(\lambda_{max} - \lambda_{min})$$

for $v \in V$ where $V=\{0, 1, \ldots, V\}$. Every rate $\lambda_{n,j}^c$ can now be approximated by $\bar{\lambda}(v_{n,j}^c)$ for some $v_{n,j}^c \in V$ that minimizes the approximation error. If a lookup table is defined with entries $L(s,v)=\log h(s,\bar{\lambda}(v))$, then (9) can be rewritten as $$\hat{x}_t = \underset{x_k^c \in \Omega}{\operatorname{argmax}} \sum_{i'=0}^{\tau'} \sum_{n=1}^{N} L(\bar{s}_{n,t'-i'}, v_{n,k-\delta-\Delta i'}^c)$$

Thus, during training, L for all s and v can be computed, in some embodiments. Similarly, $v_{n,j}^c$ for all c, n, and j can be computed during training, in some embodiments. In this way, in some embodiments, the costly process of computing log-likelihoods only needs to be performed once, during training.

The estimation procedure in (11) can be made faster still by exploiting recursive structure. Consider the following definitions:

$$q_{t,k}^c = \sum_{i'=0}^{t'} r_{t'-i',k-\delta-\Delta i'}^c$$

$$r_{j',j}^c = \begin{cases} \sum_{n=1}^{N} L(\bar{s}_{n,j'}, v_{n,j}^c) & j' > 0, j > 0 \\ 0 & \text{otherwise} \end{cases}$$

This expression can be generated recursively, $$q_{t,k}^c = \begin{cases} q_{t-\Delta,k-\Delta}^c + r_{t',k}^c - r_{t',\tau'-1,k-\tau-1}^c, & \delta = 0 \\ q_{t-1,k-1}^c, & \delta > 0 \end{cases}$$

with initial conditions $q_{t,0}^c = q_{0,k}^c = 0$. Given that $q_{t,k}^c$ is simply shifted by one index relative to previous time step when $\delta > 0$, the neural state estimate can be written as:

$$\hat{x}_t = \begin{cases} \underset{x_k^c \in \Omega}{\operatorname{argmax}} q_{t,k}^c, & \delta = 0 \\ \bar{x}_{k+\delta}^{\hat{c}}, & \delta > 0 \end{cases}$$

where $\hat{c}$ and $\hat{k}$ are the indices such that $\hat{x}_{t-\delta} = \bar{x}_{\hat{k}}^{\hat{c}}$. Note that $\hat{x}_t$ cannot be computed until $t > \tau$ (when sufficient spiking history has been collected).

The approach described in (15) is efficient insofar as it renders a new state estimate at each time t while only requiring substantial computations every $\Delta$ time samples. Nevertheless, when $\delta=0$, the recursion requires computing new $r_{t',k}^c$ and $r_{t'-\tau'-1,k-\tau-1}^c$ for every element in $\Omega_+$ to ensure that $q_{t,k}^c$ is defined for every $\bar{x}_k^c \in \Omega$. However, in some embodiments, some smoothness can be assumed over time when learning each $\omega_c$. Thus, for reasonably small $\Delta$, in some embodiments, the most likely neural state when $\delta=0$ can be approximated by only considering a subset of neural states defined by $$\tilde{\Omega} = \left\{\bar{x}_k^c \in \Omega \,\bigg|\, \frac{k}{\Delta} \in \mathbb{Z}\right\}$$

which is equivalent to downsampling the neural trajectories in $\Omega$ with $\Delta$ spacing between samples. Letting $$k' = \frac{k}{\Delta},$$

this choice yields a new expression for the neural state estimate:

$$\hat{x}_t = \begin{cases} \underset{x_k^c \in \Omega}{\operatorname{argmax}} \tilde{q}_{t',k'}^c, & \delta = 0 \\ \bar{x}_{k+\delta}^{\hat{c}}, & \delta > 0 \end{cases}$$

where $\tilde{q}_{t',k'}^c = q_{\Delta t', \Delta k'}^c$. The recursion can now be performed over fewer states:

$$\tilde{q}_{t',k'}^c = \tilde{q}_{t'-1,k'-1}^c + r_{t',\Delta k'}^c - r_{t'-\tau'-1,\Delta k'-\tau-1}^c$$

This simplification reduces memory and execution time. Furthermore, by using interpolation in some embodiments (described below), neural states outside of $\tilde{\Omega}$ can still be estimated when $\delta=0$.

The method described thus far leverages a mesh of neural states that correspond to a discrete set of time points within a discrete set of conditions. One might wish to make this mesh very fine by choosing a small ' and a large C such that small variations on a behavior each get their own $\omega_c$. However, the computational burden of the method grows as $\Delta$ shrinks or C grows. Thus, an alternative approach could involve a two-step procedure: 1) approximate the neural state using (17) and a coarse mesh; and 2) improve the estimate by considering a finer model of neural states near the coarse estimate.

Below, a method for implementing the latter via linear interpolation is described.

To consider that the current neural state may be somewhere between neural states $\bar{x}_{k_1}^{c_1}$ and $\bar{x}_{k_2}^{c_2}$, a model having the following form can be used in some embodiments:

$$\alpha \sim \text{Unif}(0,1)$$

$$x_{t-i} = (1-\alpha)\bar{x}_{k_1-i}^{c_1} + \alpha \bar{x}_{k_2-i}^{c_2}, i \in \{0, 1, \ldots, \tau\}$$

$$z_t = (1-\alpha)\bar{z}_{k_1}^{c_1} + \alpha \bar{z}_{k_2}^{c_2}$$

with the same Poisson observation model from (3). This model assumes that as the neural state smoothly varies from $\bar{x}_{k_1}^{c_1}$ to $\bar{x}_{k_2}^{c_2}$, the corresponding behavioral state smoothly varies from $\bar{z}_{k_1}^{c_1}$ to $\bar{z}_{k_2}^{c_2}$. Explicitly evaluating the probabilities associated with all possible $x_t$ in this model would be computationally expensive, but it can be shown that the log-likelihood of the observed spikes is concave with respect to $\alpha$. Thus, $\hat{\alpha}$ can be efficiently estimated using Newton-Raphson optimization and then $\hat{x}_t$ and $\hat{z}_t$ can be estimated via (20) and (21). This procedure will yield the same $\hat{\alpha}$ for all t associated with the same t'. Thus, the interpolation only needs to be performed once per time bin, when $\delta=0$.

In some embodiments, a straightforward use of the interpolation scheme described above is to interpolate between adjacent neural states along the same neural trajectory. As described above, in some embodiments, in order to reduce computational burden, the neural states that are queried can be limited to only a subset of neural states along each neural trajectory. By selecting the most probable neural state according to (17) and then interpolating with the most probable adjacent neural state, estimation with fine resolution along the neural trajectory can still be performed while retaining computational efficiency.

There are many behaviors that vary continuously and neural activity often arranges itself in an ordered fashion such that there seem to be a continuum of neural trajectories corresponding to similar conditions (actions). For example, in a cycling task in which the neural trajectories are rotational, cycling speed modulates the neural state along an axis orthogonal to the rotations, giving rise to a cylindrical neural manifold. In a situation like this, one may wish to generalize the mesh of neural trajectories into a "neural sheet" that reflects this continuity in state space. This can be accomplished in some embodiments by 1) identifying the most probable neural state in any condition (action) (and using interpolation to adjacent neural states to improve the estimate), 2) identifying the most probable neural state in any other condition (action) (also interpolating to adjacent neural states), and 3) interpolating between the neural state estimates from 1) and 2) to obtain an estimate that generalizes across the two conditions (actions). As long as the behavior of interest is represented with sufficiently similar conditions (actions) in the training set, interpolation can enable behavior to be decoded from a continuum of possibilities in some embodiments.

In some embodiments, one may occasionally wish to interpolate in a three-step (or more) process. For example, suppose a user is operating the mechanisms described herein with 10 conditions (and therefore 10 neural trajectories). If there are some neural recording instabilities, they might note that the neural trajectory for any given condition looks different depending on the state of these instabilities. Let's say there are 3 recording instability states. The user could then fit a different neural trajectory for each condition and instability state for a total of 30 neural trajectories. Let's call the set of all neural trajectories for a given instability state a "stability group". When decoding under these circumstances the user could employ a three-step interpolation: first interpolating across adjacent neural states within the same condition, then interpolating across neural states from different conditions within the same stability group, and then interpolating across neural states from different stability groups.

Turning to FIGS. 4A-4B, an example of pseudocode for a process 400 for fitting neural and behavioral trajectories in accordance with some embodiments is shown. In some embodiments, this process can be executed on a signal processor and/or computer of FIGS. 7-9.

As shown, this process receives as inputs:
$s_{n,k}^{c,tr} \forall (c,tr,n,k)$:=number of spikes observed from neuron n at time index k of trial tr of action c
$z_{m,k}^{c,tr} \forall (c,tr,m,k)$:=value of behavioral variable m at time index k of trial tr of action c
As also shown, this process outputs:
$\bar{x}_{n,k}^{c} \forall (c,n,k)$:=canonical rate for neuron n at time index k of action c
$\bar{z}_{m,k}^{c} \forall (c,m,k)$:=canonical behavioral variable m at time index k of action c The term "forall" in the pseudocode of FIGS. 4A-6D indicates that each iteration of the loop does not depend on any other iteration of the loop. Thus, the computations inside "forall" loops can be performed in parallel in some embodiments.

As illustrated, in some embodiments, process 400 in lines 1-11 filters single-trial spiking activity into smooth rates for all neurons n, in all trials tr, of all actions c.

More particularly, at line 4, the process collects spikes into a vector indexed by time indices $1 \ldots K_c$, where $K_c$ is the number of time indices in action c. In some embodiments, each time index may represent any sampling of time at a suitable period such as 1 ms.

Next, at line 5, the process filters spikes with a Gaussian and stores the results. Any suitable width of the Gaussian can be used in some embodiments, and the width used may depend on the application, in some embodiments. For example, in some embodiments, for many actions, a Gaussian with a standard deviation of 25 milliseconds can be used. As part of this filtering process, for each neuron on each trial of each action, a time-series of spikes is convolved with a zero-mean Gaussian kernel.

Then, at lines 6-8, for all time indices k, the value of rates at index k can be stored in $x_{n,k}^{c,tr}$.

As also illustrated, in some embodiments, process 400 in lines 12-21 computes the canonical rates and corresponding behavioral variables for all actions c and time indices k.

More particularly, at lines 14-16, for all neurons n, the process averages $x_{n,k}^{c,tr}$ across all trials tr for a given action c and stores the average in $\bar{x}_{n,k}^{c}$. Then, at lines 17-19, for all behavioral variables m, the process averages $z_{m,k}^{c,tr}$ across all trials tr for a given action c and stores the average in $\bar{z}_{m,k}^{c}$.

Turning to FIGS. 5A-5D, an example of pseudocode for a training process 500 in accordance with some embodiments is shown. In some embodiments, this process can be executed on a signal processor and/or computer of FIGS. 7-9.

As shown, this process receives as inputs:
$\bar{x}_{n,k}^{c} \forall (c,n,k)$:=canonical rate for neuron n at time index k of action c
$\bar{z}_{m,k}^{c} \forall (c,m,k)$:=canonical behavioral variable m at time index k of action c
These canonical rates and corresponding behavior variables (canonical behavioral variables) can be generated in any suitable manner, such as that described above in connection with FIGS. 4A-4B.
As also shown, this process provides as outputs:
$v_{n,k}^{c} \forall (c,n,k)$:=rate index for neuron n at time index k of action c
L:=lookup table whose (s, v)-th entry contains the log-liklihood of observing s spikes in a time bin from a neuron with rate index v
As further shown, this process uses the following constants:
$\Delta$:=number of time indices pooled into a time bin
$\lambda_{min}$:=minimum rate in spikes/time bin
$\lambda_{max}$:=maximum rate in spikes/time bin
V:=constant value determining how rates are sampled between $\lambda_{min}$ and $\lambda_{max}$ For notational simplicity, variables throughout the pseudocode are written in indexed form where c indexes condition (action), tr indexes trial number, n indexes neurons, m indexes behavioral variables, and k indexes time within each condition (action). These indices are integers that vary over finite ranges and the maximum values they attain are determined by the training data and/or set explicitly by the user. For example, the total number of conditions (actions) will be determined by the tasks the user collected training data for and how the user has chosen to sort these trials into different conditions (actions) in some embodiments.

Neural rates are often reported in units of spikes/second. However, throughout this pseudocode one should assume all neural rates are in units of spikes/time bin.

The process can begin by receiving inputs $\bar{x}_{n,k}^c$ and $\bar{z}_{n,k}^c$ for all conditions (actions) c, trials tr, neurons n, behavioral variables m, and time indices k. As described above, in some embodiments, these can be generated in any suitable manner, such as using the process described in connection with FIGS. 4A-4B.

Next, at lines 1-3, for all rate indices $v$ from zero to V, the process determines a particular rate that corresponds to each rate index $v$.

The constants $\lambda_{min}$, $\lambda_{max}$, and V are all set ahead of time by the user in some embodiments. In some embodiments, $\lambda_{min}$ should be set to a small positive number (e.g., 1 spike/second) that balances the desire to allow low rates along neural trajectories with the understanding that it can be difficult to accurately estimate low rates from a small amount of training data (and very low-rate estimates may harm results by assigning exceptionally small likelihoods to spiking events under a Poisson observation model). In some embodiments, $\lambda_{max}$ should be set to the largest rate one expects to ever encounter. In some embodiments, V should be set to ensure the range $[\lambda_{min}, \lambda_{max}]$ is sampled reasonably finely (e.g., at least one sample every 0.5 spikes/second). Although the rates in this paragraph are described in spikes/second, the actual values for $\lambda_{min}$ and $\lambda_{max}$ need to be in units of spikes/time bin for the process described in connection with FIGS. 5A-5D.

Then, at lines 4-12, for all actions c, all neurons n, and time indices k, the process learns the rate indices for the neural states in the library of neural trajectories.

Although the pseudocode is written to compute $v_{n,k}^c$ for every time index k, in some embodiments only values for which k is a multiple of $\Delta$ will get used in decoding. Thus, in some embodiments, only these values actually need to be computed. Nevertheless, the pseudocode is written this way to best match the notation used elsewhere herein.

Next, at lines 13-17, for all possible spike counts s and for all rate indices $v$, a lookup table for the log-likelihood of observing s spikes in a time bin from a neuron with rate $\tilde{\lambda}(v)$ given a Poisson observation model is built. The lookup table uses zero-based indexing in some embodiments.

Note that the number of possible spikes observed within each time bin for any given neuron is limited. Due to the physiological properties of neurons, they can only emit spikes so rapidly. As a rule of thumb, one can expect to never observe more than one spike per millisecond from any neuron, in some embodiments.

Turning to FIGS. 6A-6D, an example of pseudocode for a process 600 for online decoding in accordance with some embodiments is shown. In some embodiments, this process can be executed on a signal processor and/or computer of FIGS. 7-9.

As shown, this process uses the following observations:
$s_{n,t} \forall (n,t)$:=number of spikes observed from neuron n at time t As also shown, the process decodes the following variables:
$\hat{x}_{n,t} \forall (n,t)$:=decoded state of neuron n at time t
$\hat{z}_{m,t} \forall (m,t)$:=decoded behavioral variable m at time t As further shown, the process uses the following parameters:
$\bar{x}_{n,k}^c \forall (c,n,k)$:=canonical rate for neuron n at time index k of action c
$\bar{z}_{m,k}^c \forall (c,m,k)$:=canonical behavioral variable m at time index k of action c
$v_{n,k}^c \forall (c,n,k)$:=rate index for neuron n at time index k of action c
L:=lookup table whose (s, $v$)-th entry contains the log-likelihood of observing s spikes in a time bin from a neuron with rate index $v$ As still further shown, the process uses the following constants:
$\Delta$:=number of time indices pooled into a time bin
$\tau'$:=number of previous time bins of spiking activity (in addition to the current time bins to use in decoding
$\tau = \Delta(\tau'+1)-1$ There are several indices that refer to time in this pseudocode. t indicates the present decoding time at sample resolution and t' indicates the present decoding time at bin resolution. k indexes time along the neural and behavioral trajectories at sample resolution and k' indexes time along the neural and behavioral trajectories at bin resolution. Critically, although k and k' corresponded to times in the training data, they are now best thought of simply as indices to locations along learned trajectories. That is, t and t' indicate actual time while decoding whereas k and k' do not.

As shown in FIG. 6A, at lines 1-2, process 600 initializes variables t and $\tilde{q}_{0,k'}^c$. More particularly, at line 1, the process sets t equal to zero. At line 2, the process sets $\tilde{q}_{0,k'}^c$ equal to zero for all k', where k' indexes time bins along neural and behavioral trajectories, i.e., $k'=k/\Delta$ for k that is a multiple of $\Delta$.

Next, at lines 3-32, the process loops for each time sample t, which increments with each loop.

In lines 5-22, for each bin, the process first determines the bin number t' at line 6 and then sums the number of spikes observed for each neuron over the time samples in the bin in lines 7-9.

Then, at lines 12-20, for all actions c and time bin indices k' along each action c, the process uses recursion to compute log-likelihoods. Note that the last additive term in the recursion is not well-defined if $t' \leq \tau'+1$ or $k' \leq \tau'+1$. By defining the term to equal zero in either of these cases, this issue is resolved and the recursion yields the correct values.

The computations performed for each c are independent of one another. Thus, these computations can be performed simultaneously on parallel processors to speed up real-time execution in some embodiments.

Next, at line 21, the process can select the most probable action $\hat{c}$ and time bin index $\hat{k}'$. More particularly, the process can select the pair of values (c, k') that maximizes $\tilde{q}_{t',k'}^c$ subject to the constraint $\hat{k}' > \tau'$.

At lines 23-31, after sufficient spiking history has accumulated at the start of a decoding session (i.e., $t > \tau$), the process determines the decoded state of neuron n at time t, $\hat{x}_{n,t}$, and the decoded behavioral variable m at time t, $\hat{z}_{m,t}$.

As long at this process is decoding, the process can loop back to line 3, otherwise the process can end at line 32.

In accordance with some embodiment, as described above, a decoding process that is able to accurately estimate a behavior (e.g., movement, speech, cursor control, robotic limb command, wheelchair command, etc.) in real time based on measurements of neural activity is provided. In accordance with some embodiments, neural activity can be captured in any suitable manner. For example, for muscle recordings in a healthy subject, this might consist of an electromyography cuff with associated hardware. In some embodiments, any suitable device can be used to enact desired behavior. For example, in some embodiments, if one wished to restore movement in a paralyzed human patient, the following selections might be used: 1) Utah arrays for recording neural activity directly from motor cortex (all hardware commercially available from Blackrock Microsystems of Salt Lake City, Utah); and 2) a robotic prosthetic exoskeleton capable of moving in response to an incoming stream of UDP packets encoding behavioral commands.

While specific examples of neural recording equipment capable of detecting and storing individual neural spikes from a collection of neurons (or multi-units) at a fine time resolution (e.g., millisecond sampling) are described herein, it should be apparent to one of ordinary skill in the art that any suitable equipment from any suitable source can be used in some embodiments.

Below are more specific examples of hardware that can be used in some embodiments.

Figure 7:
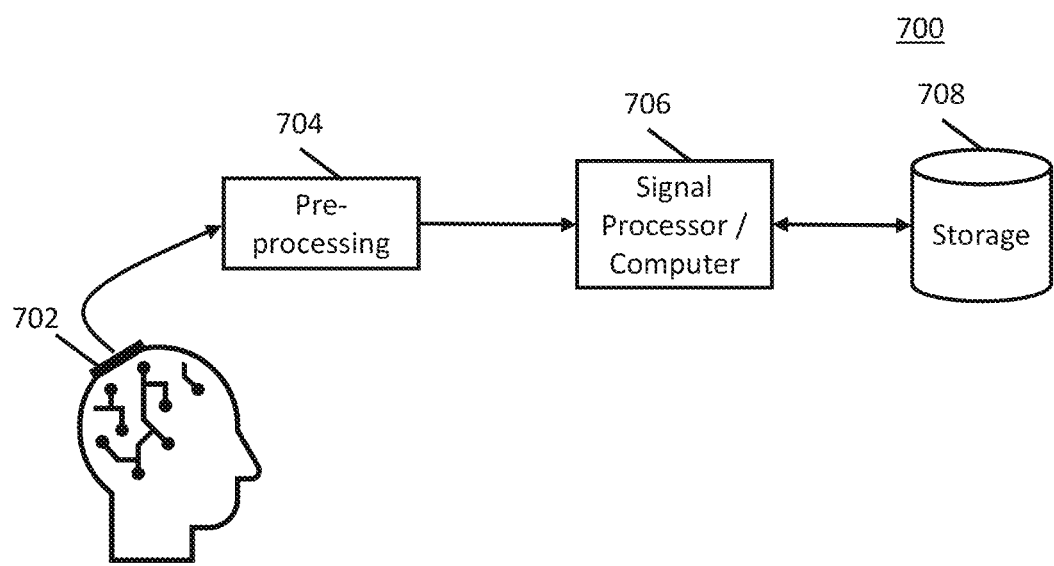
FIG. 7 is an example of system hardware that can be used in accordance with some embodiments.
Figure 8:
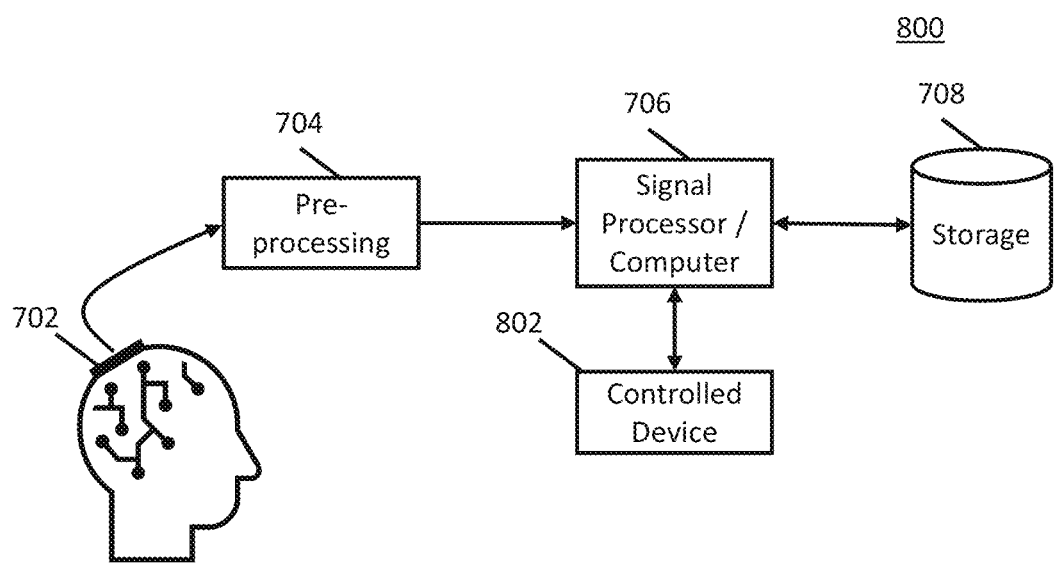
FIG. 8 is another example of system hardware that can be used in accordance with some embodiments.
Figure 9:
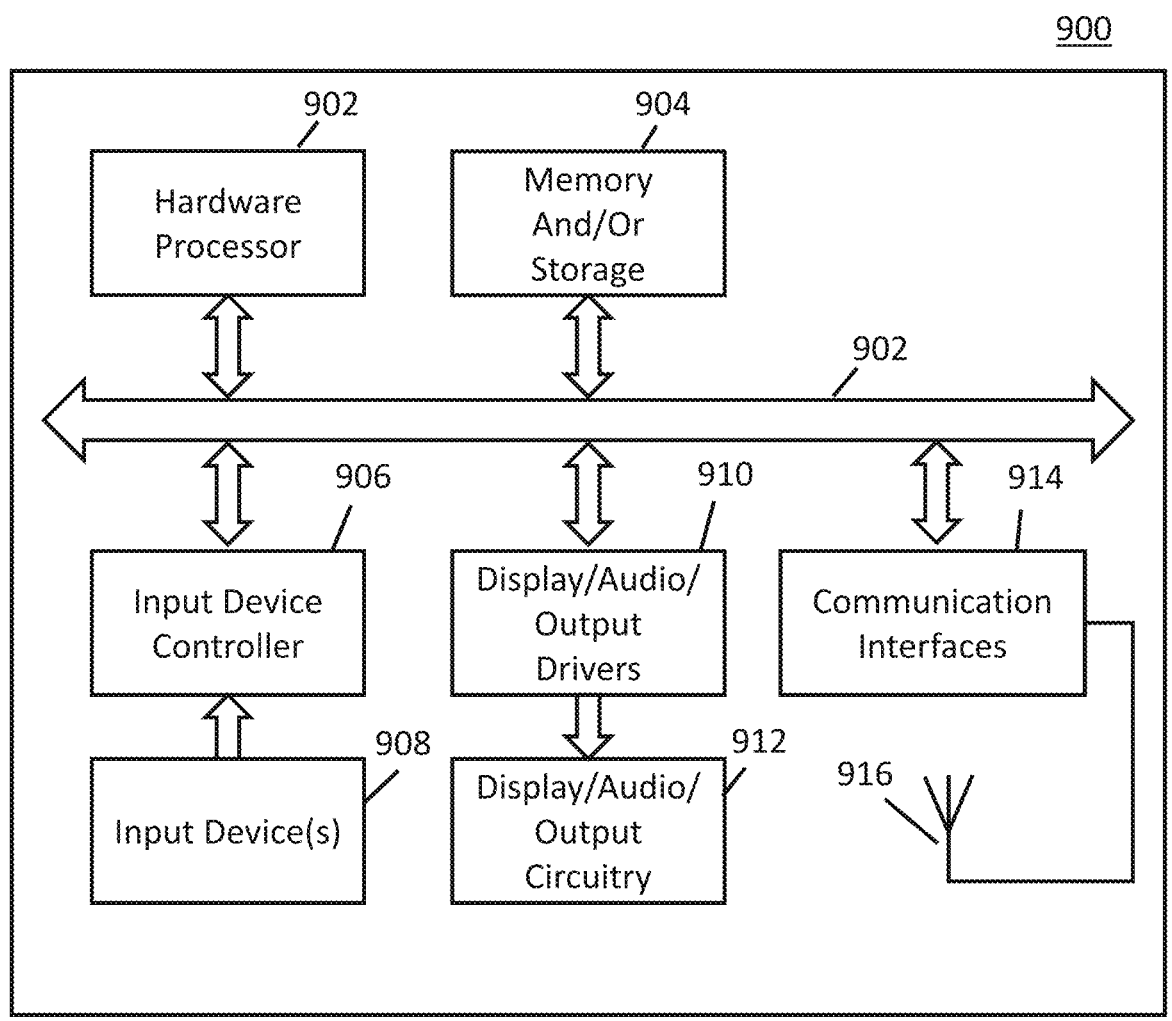
FIG. 9 is an example of computer hardware that can be used in accordance with some embodiments.

Turning to FIGS. 7 and 8, examples of hardware configurations 700 and 800 are shown. As shown in FIG. 7, an example of a hardware configuration 700 suitable for training and/or monitoring of a subject is illustrated. As shown in FIG. 8, an example of a hardware configuration 800 suitable for training, monitoring of a subject, and/or controlling a device is illustrated.

As shown, each of configurations 700 and 800 include subject interface hardware 702 for interfacing with a subject. Subject interface hardware 702 can be any suitable hardware. For example, for muscle recordings in a healthy subject, this might consist of an electromyography cuff with associated hardware. As another example, in some embodiments, hardware 702 may include any suitable number (e.g., two) of Utah arrays (available from Blackrock Microsystems of Salt Lake City, Utah), each including any suitable number (e.g., 96 or 128) electrodes arranged in any suitable shape (e.g., a grid), which can be surgically implanted in the surface of a subject's motor cortex (or otherwise exposed to the subject's neurons), with gold wires (or any other suitable conduits for carrying signals) carrying the raw electrode voltages out of the brain, through the skull, and to any suitable strain-relieving electrical interface (e.g., such as a head-mounted CerePort Pedestal, which serves as a connector). Any other suitable sensor(s) and wires can be additionally or alternatively used in some embodiments.

In some embodiments, a pre-processing unit 704 can be positioned close to hardware 702 in order to perform initial processing on the signals detected by hardware 702. For example, in some embodiments, a CerePort Pedestal (available from Blackrock Microsystems of Salt Lake City, Utah) forming part of hardware 702 can pass the raw voltages to a CerePlex E256, which mates directly with the pedestal, and which can act as a pre-processing unit 704. Any other suitable connectors can be additionally or alternatively used in some embodiments. In some such embodiments, the CerePlex E256 (available from Blackrock Microsystems of Salt Lake City, Utah) receives voltages from the CerePort Pedestal (one voltage per electrode) and filters, amplifies, and digitizes these signals at a sampling rate of 30 kHz. By performing these signal processing steps close to the recording site, signal artifacts and noise are reduced. Any other suitable filters, amplifiers, and digitizers can be additionally or alternatively used in some embodiments.

In some embodiments, the processed signals can then be transmitted digitally to one or two digital hubs (not shown), each of which can receive the data from one array. The digital hubs (available from Blackrock Microsystems of Salt Lake City, Utah) can receive digital inputs from the CerePlex E256 and convert them to an optical-digital format, which allows the signals to be transmitted longer distances without introducing substantial noise. Any other suitable device for converting the digital signals to optical signals can be additionally or alternatively used in some embodiments. In some embodiments, converting the digital signals to optical signals can be omitted.

As shown in FIGS. 7 and 8, a signal processor/computer 706 can then receive the outputs of pre-processing unit 704 and perform that data collection, training, and decoding processes, as well as any other suitable functions, as described herein. Any suitable one or more signal processing devices and/or computers can be used to implement signal processor/computer 706 in some embodiments. For example, at least part of signal processor/computer 706 can be implemented using one or more Cerebus Neural Signal Processors (available from Blackrock Microsystems of Salt Lake City, Utah).

Signal processor/computer 706 can perform any suitable processing in some embodiments. For example, the follow processing steps could be applied to each electrode channel: 1) filter the signal with a digital highpass filter with a cutoff frequency of 250 Hz, 2) set a voltage threshold that is between −4.5 and −3 times the root-mean-square voltage on that channel, 3) declare an action potential (or 'spike') has been detected each time the voltage drops below this threshold.

Signal processor/computer 706 can additionally or alternatively include any suitable one or more computers (e.g., a "training computer" and a "decoding computer") that can be used to implement one or more of the functions described herein. The Cerebus Neural Signal Processors can additionally receive other analog and digital inputs carrying measured behavioral variables during the training stage and transmit them to the one or more computers (e.g., the "training computer"). Any other suitable filters, comparators (for thresholding and declaring spike times), and transmitters can be additionally or alternatively used in some embodiments.

As also shown in FIGS. 7 and 8, any suitable external storage 708 may also be provided for storing data and/or programs used by signal processor/computer 706 in some embodiments. In some embodiments, storage 708 can be omitted.

As shown in FIG. 8, in some embodiments, any suitable controlled device 802 can also be provided. Device 802 can be any suitable device that can be used to implement desired actions. For example, in some embodiments, device 802 can be a prosthetic device (e.g., arm, leg, hand, foot, finger, toe, etc.), a wheelchair, a voice synthesizer, a computer, a computer input device, a remote control, and/or any other suitable device that a subject may wish to control. As described herein, controlled device 802 can be controlled by signal processor/computer 706 based on the estimated behavioral variables output by the decoding process.

As described herein, a training computer and a decoding computer, or a combined training/decoding computer can be used to perform functions as described in accordance with some embodiments. Any suitable general-purpose computer or special purpose computer can be used as a training computer, a decoding computer, or a combined training/decoding computer in some embodiments.

Any such general-purpose computer or special purpose computer can include any suitable hardware, in some embodiments. For example, as illustrated in example hardware 900 of FIG. 9, such hardware can include a hardware processor 902, memory and/or storage 904, an input device controller 906, an input device 908, display/audio/output drivers 910, display/audio/output circuitry 912, communication interface(s) 914, an antenna 916, and a bus 918.

Hardware processor 902 can include any suitable hardware processor, such as a microprocessor, a micro-controller, a digital signal processor, dedicated logic, and/or any other suitable circuitry for controlling the functioning of a general-purpose computer or a special purpose computer in some embodiments. In some embodiments, multiple hardware processors 902 can be included to facilitate parallel processing as described herein.

Memory and/or storage 904 can be any suitable memory and/or storage for storing data, lookup tables, programs, etc. in some embodiments. For example, memory and/or storage 904 can include random access memory, read-only memory, flash memory, hard disk storage, optical media, etc.

Input device controller 906 can be any suitable circuitry for controlling and receiving input from one or more input devices 908 in some embodiments. For example, input device controller 906 can be circuitry for receiving input from a touch screen, from one or more buttons, from a voice recognition circuit, from a microphone, from a camera, from an optical sensor, from an accelerometer, from a temperature sensor, from a force sensor, from a near field sensor, a brain interface sensor, a muscle sensor, a nerve sensor, etc.

Display/audio/output drivers 910 can be any suitable circuitry for controlling and driving output to one or more display/audio/output circuitries 912 in some embodiments. For example, display/audio drivers 910 can be circuitry for driving an LCD display, a speaker, an LED, an industrial robot, a robotic arm, a robotic leg, a robotic hand, a robotic exoskeleton, a wheelchair, a stimulator, etc.

Communication interface(s) 914 can be any suitable circuitry for interfacing with one or more communication networks, in some embodiments. For example, interface(s) 914 can include network interface card circuitry, wireless communication circuitry, etc.

Antenna 916 can be any suitable one or more antennas for wirelessly communicating with a communication network in some embodiments. In some embodiments, antenna 916 can be omitted when not needed.

Bus 918 can be any suitable mechanism for communicating between two or more components 902, 904, 906, 910, and 914 in some embodiments.

Any other suitable components can be included in hardware 900, and any un-needed components of hardware 900 can be omitted, in accordance with some embodiments.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read-only memory (EPROM), electrically erasable programmable read-only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A method of decoding observed spike counts for spiking cells, comprising:
    receiving a first set of observed spike counts for the spiking cells;
    determining a set of probabilities by:
        retrieving the set of probabilities from stored information; or
        calculating the set of probabilities based on the stored information,
        wherein the stored information regards possible biological states of a subject,
        wherein each of the possible biological states belongs to at least one of a plurality of time sequences of biological states,
        wherein each of the plurality of time sequences of biological states corresponds to a possible action of the subject, and
        wherein each probability in the set of probabilities indicates a likelihood of observing a possible spike count for one of the plurality of spiking cells;
    identifying using a hardware processor a first identified biological state of the subject from the possible biological states based on the first set of observed spike counts and the set of probabilities, wherein the identifying of the first identified biological state of the subject comprises:
    for each of the possible biological states in each of the plurality of time sequences of biological states:
        retrieving or calculating a spiking cell probability for each of the spiking cells by matching the first set of observed spike counts to corresponding stored information for the possible biological state; and
        calculating a combined probability that the first set of spike counts corresponds to the possible biological state based on a combination of the spiking cell probabilities;
    determining an action to be performed based on the first identified biological state; and
    causing the action to be performed.

2. The method of claim 1, wherein the action is to cause at least a portion of the subject, or a device controlled by the subject, to move relative to space around the subject.

3. The method of claim 1, wherein the action is to indicate an internal state of the brain of the subject.

4. The method of claim 1, wherein the identifying of the first identified biological state of the subject comprises identifying the first identified biological state based on the first set of observed spike counts, the set of probabilities, and a utility function.

5. The method of claim 1, further comprising:
    identifying a second identified biological state of the subject from the possible biological states based on the first set of observed spike counts and the set of probabilities; and
    determining a third identified biological state from at least the first identified biological state and the second identified biological state.

6. The method of claim 1, wherein the spiking cells are muscle cells.

7. The method of claim 1, further comprising:
    receiving a subsequent set of observed spike counts for the spiking cells, wherein the subsequent set of observed spike counts are observed at a different time than the first set of observed spike counts are observed; and identifying a subsequent identified biological state of the subject from the possible biological states based on the subsequent set of observed spike counts, the first set of observed spike counts, and the set of probabilities.

8. The method of claim 1, wherein the probabilities are log-probabilities.

9. A system for decoding observed spike counts for spiking cells, comprising:
a memory; and
a hardware processor coupled to the memory and configured to:
receive a first set of observed spike counts for the spiking cells;
determine a set of probabilities by:
retrieving the set of probabilities from stored information; or
calculating the set of probabilities based on the stored information,
wherein the stored information regards possible biological states of a subject,
wherein each of the possible biological states belongs to at least one of a plurality of time sequences of biological states,
wherein each of the plurality of time sequences of biological states corresponds to a possible action of the subject, and
wherein each probability in the set of probabilities indicates a likelihood of observing a possible spike count for one of the plurality of spiking cells;
identify a first identified biological state of the subject from the possible biological states based on the first set of observed spike counts and the set of probabilities, wherein the identifying of the first identified biological state of the subject comprises:
for each of the possible biological states in each of the plurality of time sequences of biological states:
retrieving or calculating a spiking cell probability for each of the spiking cells by matching the first set of observed spike counts to corresponding stored information for the possible biological state; and
calculating a combined probability that the first set of spike counts corresponds to the possible biological state based on a combination of the spiking cell probabilities;
determine an action to be performed based on the first identified biological state; and
cause the action to be performed.

10. The system of claim 9, wherein the action is to cause at least a portion of the subject, or a device controlled by the subject, to move relative to space around the subject.

11. The system of claim 9, wherein the action is to indicate an internal state of the brain of the subject.

12. The system of claim 9, wherein the identifying of the first identified biological state of the subject comprises identifying the first identified biological state based on the first set of observed spike counts, the set of probabilities, and a utility function.

13. The system of claim 9, wherein the hardware processor is further configured to:

identifying a second identified biological state of the subject from the possible biological states based on the first set of observed spike counts and the set of probabilities; and determining a third identified biological state from at least the first identified biological state and the second identified biological state.

14. The system of claim 9, wherein the spiking cells are muscle cells.

15. The system of claim 9, wherein the hardware processor is further configured to:
receiving a subsequent set of observed spike counts for the spiking cells, wherein the subsequent set of observed spike counts are observed at a different time than the first set of observed spike counts are observed; and
identifying a subsequent identified biological state of the subject from the possible biological states based on the subsequent set of observed spike counts, the first set of observed spike counts, and the set of probabilities.

16. The system of claim 9, wherein the probabilities are log-probabilities.

17. A non-transitory computer-readable medium containing computer executable instructions that, when executed by a processor, cause the processor to perform a method of decoding observed spike counts for spiking cells, the method comprising:
receiving a first set of observed spike counts for the spiking cells;
determining a set of probabilities by:
retrieving the set of probabilities from stored information; or
calculating the set of probabilities based on the stored information,
wherein the stored information regards possible biological states of a subject,
wherein each of the possible biological states belongs to at least one of a plurality of time sequences of biological states,
wherein each of the plurality of time sequences of biological states corresponds to a possible action of the subject, and
wherein each probability in the set of probabilities indicates a likelihood of observing a possible spike count for one of the plurality of spiking cells;
identifying a first identified biological state of the subject from the possible biological states based on the first set of observed spike counts and the set of probabilities, wherein the identifying of the first identified biological state of the subject comprises:
for each of the possible biological states in each of the plurality of time sequences of biological states:
retrieving or calculating a spiking cell probability for each of the spiking cells by matching the first set of observed spike counts to corresponding stored information for the possible biological state; and
calculating a combined probability that the first set of spike counts corresponds to the possible biological state based on a combination of the spiking cell probabilities;
determining an action to be performed based on the first identified biological state; and causing the action to be performed.

18. The non-transitory computer-readable medium of claim 17, wherein the action is to cause at least a portion of the subject, or a device controlled by the subject, to move relative to space around the subject.

19. The non-transitory computer-readable medium of claim 17, wherein the action is to indicate an internal state of the brain of the subject.

20. The non-transitory computer-readable medium of claim 17, wherein the identifying of the first identified biological state of the subject comprises identifying the first identified biological state based on the first set of observed spike counts, the set of probabilities, and a utility function.

21. The non-transitory computer-readable medium of claim 17, wherein the method further comprises:
   identifying a second identified biological state of the subject from the possible biological states based on the first set of observed spike counts and the set of probabilities; and
   determining a third identified biological state from at least the first identified biological state and the second identified biological state.

22. The non-transitory computer-readable medium of claim 17, wherein the spiking cells are muscle cells.

23. The non-transitory computer-readable medium of claim 17, wherein the method further comprises:
   receiving a subsequent set of observed spike counts for the spiking cells, wherein the subsequent set of observed spike counts are observed at a different time than the first set of observed spike counts are observed; and
   identifying a subsequent identified biological state of the subject from the possible biological states based on the subsequent set of observed spike counts, the first set of observed spike counts, and the set of probabilities.

24. The non-transitory computer-readable medium of claim 17, wherein the probabilities are log-probabilities.

* * * * *

UNITED STATES PATENT AND TRADEMARK OFFICE
CERTIFICATE OF CORRECTION

| | |
|---|---|
| PATENT NO. | : 11,429,847 B2 |
| APPLICATION NO. | : 17/589716 |
| DATED | : August 30, 2022 |
| INVENTOR(S) | : Sean Perkins et al. |

It is certified that error appears in the above-identified patent and that said Letters Patent is hereby corrected as shown below:

In the Specification

Column 9, Line 13, "even if each neuron's rate is divided into only $10^{1280}$, there are" should be --even if each neuron's rate is divided into only 10 bins, there are--.

Signed and Sealed this
Twenty-third Day of May, 2023

Katherine Kelly Vidal
*Director of the United States Patent and Trademark Office*